(12) United States Patent
Whittaker et al.

(10) Patent No.: US 10,639,085 B2
(45) Date of Patent: May 5, 2020

(54) METHODS, DEVICES, AND SYSTEMS FOR BLOOD FLOW

(71) Applicant: Medos International Sarl, Le Locle (CH)

(72) Inventors: Gregory R. Whittaker, Stoneham, MA (US); Benjamin Cleveland, Weymouth, MA (US); Julia Hwang, Wayland, MA (US); David B. Spenciner, North Attleboro, MA (US); William R. Parrish, Hudson, MA (US); Mehmet Z. Sengun, Canton, MA (US); Reagan A. Theis, Marshfield, MA (US)

(73) Assignee: MEDOS INTERNATIONAL SARL, Le Locle (CH)

( * ) Notice: Subject to any disclaimer, the term of this patent is extended or adjusted under 35 U.S.C. 154(b) by 0 days.

(21) Appl. No.: 15/838,781

(22) Filed: Dec. 12, 2017

(65) Prior Publication Data

US 2018/0098803 A1    Apr. 12, 2018

Related U.S. Application Data

(62) Division of application No. 15/148,464, filed on May 6, 2016, now Pat. No. 9,861,410.

(51) Int. Cl.
*A61B 17/84*    (2006.01)
*A61B 17/04*    (2006.01)
(Continued)

(52) U.S. Cl.
CPC ........ *A61B 17/846* (2013.01); *A61B 17/0401* (2013.01); *A61L 27/28* (2013.01);
(Continued)

(58) Field of Classification Search
None
See application file for complete search history.

(56) References Cited

U.S. PATENT DOCUMENTS 3,987,797 A    10/1976    Stephenson
4,006,743 A    2/1977    Kowarski
(Continued)

FOREIGN PATENT DOCUMENTS

WO    WO-0178799 A1    10/2001

OTHER PUBLICATIONS

U.S. Appl. No. 15/148,464, U.S. Pat. No. 9,861,410, filed May 6, 2016, Methods, Devices and Systems for Blood Flow.
(Continued)

*Primary Examiner* — Robert A Wax
*Assistant Examiner* — Melissa S Mercier (57) ABSTRACT

Various exemplary methods, systems, and devices for blood flow are provided. In general, an implant can be configured to be implanted in bone and to delay clotting of blood flowing from the bone. The implant can include an anti-coagulation agent to delay the clotting of the blood. The anti-coagulation agent can be a coating on the implant, can be natural to a material forming the implant, or can be impregnated into a material forming the implant. In an exemplary embodiment, the implant is implanted in a bone in a surgical procedure for securing a soft tissue to bone, such as a rotator cuff repair procedure or an anterior cruciate ligament (ACL) repair procedure.

15 Claims, 3 Drawing Sheets

(51) Int. Cl.
  *A61L 27/28* (2006.01)
  *A61L 27/34* (2006.01)
  *A61L 27/58* (2006.01)
  *A61M 25/00* (2006.01)
  *A61B 17/00* (2006.01)
  *A61B 17/56* (2006.01)

(52) U.S. Cl.
  CPC ............ *A61L 27/34* (2013.01); *A61L 27/58* (2013.01); *A61M 25/0043* (2013.01); *A61B 2017/00004* (2013.01); *A61B 2017/044* (2013.01); *A61B 2017/045* (2013.01); *A61B 2017/0412* (2013.01); *A61B 2017/0445* (2013.01); *A61B 2017/0458* (2013.01); *A61B 2017/561* (2013.01); *A61L 2300/42* (2013.01); *A61L 2430/02* (2013.01); *A61M 2025/0057* (2013.01)

(56) References Cited

U.S. PATENT DOCUMENTS

| | | | |
|---|---|---|---|
| 4,905,671 A | 3/1990 | Senge et al. | |
| 5,171,264 A | 12/1992 | Merrill | |
| 5,226,914 A | 7/1993 | Caplan et al. | |
| 5,342,621 A | 8/1994 | Eury | |
| 5,681,289 A | 10/1997 | Wilcox et al. | |
| 5,702,422 A | 12/1997 | Stone | |
| 5,860,978 A | 1/1999 | McDevitt et al. | |
| 5,868,720 A | 2/1999 | Van Antwerp | |
| 5,891,101 A | 4/1999 | Wilcox et al. | |
| 5,895,375 A | 4/1999 | Wilcox et al. | |
| 5,964,767 A * | 10/1999 | Tapia | A61B 17/3421 411/177 |
| 6,083,522 A * | 7/2000 | Chu | A61B 17/0401 424/423 |
| 6,096,060 A | 8/2000 | Fitts et al. | |
| 6,142,939 A | 11/2000 | Eppstein et al. | |
| 6,156,056 A | 12/2000 | Kearns et al. | |
| RE37,107 E | 3/2001 | Wells-Roth | |
| 6,197,036 B1 | 3/2001 | Tripp et al. | |
| 6,197,043 B1 | 3/2001 | Davidson | |
| 6,332,889 B1 | 12/2001 | Sancoff et al. | |
| 6,350,251 B1 | 2/2002 | Prosl et al. | |
| 6,413,216 B1 | 7/2002 | Cain et al. | |
| 6,511,444 B2 | 1/2003 | Hynynen et al. | |
| 6,685,657 B2 | 2/2004 | Jones | |
| 6,689,153 B1 * | 2/2004 | Skiba | A61B 17/0401 606/230 |
| 6,727,224 B1 | 4/2004 | Zhang et al. | |
| 6,737,053 B1 | 5/2004 | Goh et al. | |
| 6,811,777 B2 | 11/2004 | Mishra | |
| 6,814,741 B2 | 11/2004 | Bowman et al. | |
| 6,969,525 B2 | 11/2005 | Chow | |
| 6,991,635 B2 | 1/2006 | Takamoto et al. | |
| 7,063,710 B2 | 6/2006 | Takamoto et al. | |
| 7,137,996 B2 | 11/2006 | Steiner et al. | |
| 7,163,563 B2 | 1/2007 | Schwartz et al. | |
| 7,189,209 B1 | 3/2007 | Ogden et al. | |
| 7,201,773 B2 | 4/2007 | Steiner et al. | |
| 7,309,356 B2 | 12/2007 | Steiner | |
| 7,470,240 B2 | 12/2008 | Schultheiss et al. | |
| 7,601,525 B2 | 10/2009 | Batich et al. | |
| 7,608,258 B2 | 10/2009 | Mishra | |
| 7,691,839 B2 | 4/2010 | Glidden | |
| 7,766,915 B2 * | 8/2010 | Jackson | A61B 17/7028 606/86 A |
| 7,776,039 B2 | 8/2010 | Bernstein et al. | |
| 7,785,582 B2 | 8/2010 | Johnson | |
| 7,789,841 B2 | 9/2010 | Huckle et al. | |
| 7,837,708 B2 | 11/2010 | Schmieding et al. | |
| 7,850,983 B2 | 12/2010 | Sevrain et al. | |
| 7,871,440 B2 | 1/2011 | Schwartz et al. | |
| 7,918,854 B2 | 4/2011 | Schwartz | |
| 7,985,189 B1 | 7/2011 | Ogden et al. | |
| 7,988,716 B2 | 8/2011 | Schwartz | |
| 8,012,174 B2 | 9/2011 | ElAttrache et al. | |
| 8,048,042 B2 | 11/2011 | Ogle et al. | |
| 8,070,810 B2 | 12/2011 | Tarrant et al. | |
| 8,114,128 B2 | 2/2012 | Cauldwell et al. | |
| 8,123,707 B2 | 2/2012 | Huckle et al. | |
| 8,133,268 B2 | 3/2012 | Bonsignore | |
| 8,153,112 B2 | 4/2012 | Drapeau et al. | |
| 8,178,084 B2 | 5/2012 | Smith et al. | |
| 8,188,034 B2 | 5/2012 | Glidden | |
| 8,211,017 B2 | 7/2012 | Foley et al. | |
| 8,221,496 B2 | 7/2012 | Zhao | |
| 8,257,963 B2 | 9/2012 | Binette et al. | |
| 8,258,117 B2 | 9/2012 | Hoemann et al. | |
| 8,298,560 B2 | 10/2012 | Sevrain et al. | |
| 8,343,051 B2 | 1/2013 | Desilets et al. | |
| 8,343,480 B2 | 1/2013 | Long et al. | |
| 8,383,156 B2 | 2/2013 | Zhao | |
| 8,419,794 B2 | 4/2013 | ElAttrache et al. | |
| 8,475,505 B2 | 7/2013 | Nebosky et al. | |
| 8,535,377 B2 | 9/2013 | Myers et al. | |
| 8,579,947 B2 | 11/2013 | Wu | |
| 8,579,975 B2 | 11/2013 | Myers | |
| 8,592,201 B2 | 11/2013 | Story et al. | |
| 8,597,336 B2 | 12/2013 | van der Burg et al. | |
| 8,617,241 B2 | 12/2013 | Myers | |
| 8,637,066 B2 | 1/2014 | Binnette et al. | |
| 8,691,946 B2 | 4/2014 | Sanford et al. | |
| 8,702,754 B2 | 4/2014 | DiMatteo et al. | |
| 8,702,767 B2 | 4/2014 | Nebosky et al. | |
| 8,702,796 B2 | 4/2014 | Myers | |
| 8,728,495 B2 | 5/2014 | Sevrain et al. | |
| 8,740,987 B2 | 6/2014 | Geremakis et al. | |
| 8,771,351 B2 | 7/2014 | ElAttrache et al. | |
| 8,771,672 B2 | 7/2014 | Callegaro et al. | |
| 8,785,191 B2 | 7/2014 | Mazzocca et al. | |
| 8,858,560 B2 | 10/2014 | Bradley et al. | |
| 8,871,199 B2 | 10/2014 | Centeno | |
| 8,876,864 B2 | 11/2014 | Spedden et al. | |
| 9,127,091 B2 | 9/2015 | Luthra et al. | |
| 9,138,317 B2 | 9/2015 | McGee | |
| 9,180,089 B2 | 11/2015 | Buckley et al. | |
| 9,743,961 B2 * | 8/2017 | Goel | A61B 17/68 |
| 9,861,410 B2 | 1/2018 | Whittaker et al. | |
| 2003/0088252 A1 | 5/2003 | Kaikkonen et al. | |
| 2003/0118563 A1 | 6/2003 | Loeb | |
| 2003/0158598 A1 | 8/2003 | Ashton et al. | |
| 2004/0034357 A1 | 2/2004 | Beane et al. | |
| 2004/0260318 A1 | 12/2004 | Hunter et al. | |
| 2005/0251180 A1 | 11/2005 | Burton et al. | |
| 2006/0039896 A1 | 2/2006 | Kleinsek et al. | |
| 2006/0051328 A1 | 3/2006 | Johnson | |
| 2006/0093646 A1 | 5/2006 | Cima et al. | |
| 2006/0222756 A1 | 10/2006 | Davila et al. | |
| 2006/0280768 A1 | 12/2006 | Hwang et al. | |
| 2007/0016163 A1 | 1/2007 | Santini et al. | |
| 2007/0055255 A1 | 3/2007 | Siegel | |
| 2008/0027470 A1 | 1/2008 | Hart et al. | |
| 2008/0071198 A1 | 3/2008 | Ogden et al. | |
| 2008/0188936 A1 | 8/2008 | Ball et al. | |
| 2008/0234730 A1 | 9/2008 | Cotton et al. | |
| 2009/0060975 A1 | 3/2009 | Teets et al. | |
| 2009/0130167 A1 | 5/2009 | Shelton et al. | |
| 2009/0157193 A1 | 6/2009 | McKay | |
| 2009/0177085 A1 | 7/2009 | Maxwell et al. | |
| 2009/0177229 A1 | 7/2009 | Gulotta et al. | |
| 2009/0187216 A1 | 7/2009 | Schmieding et al. | |
| 2009/0306776 A1 | 12/2009 | Murray | |
| 2009/0318837 A1 | 12/2009 | Desilets | |
| 2010/0042213 A1 | 2/2010 | Nebosky et al. | |
| 2010/0042214 A1 | 2/2010 | Nebosky et al. | |
| 2010/0130959 A1 | 5/2010 | Boyd et al. | |
| 2010/0152831 A1 | 6/2010 | Guo et al. | |
| 2010/0179589 A1 | 7/2010 | Roorda et al. | |
| 2010/0285094 A1 | 11/2010 | Gupta | |
| 2011/0153000 A1 | 6/2011 | Schwartz | |
| 2012/0010727 A1 | 1/2012 | Young et al. | |
| 2012/0071920 A1 | 3/2012 | Shanley et al. | |
| 2012/0071921 A1 | 3/2012 | Shanley et al. | |

(56) References Cited

U.S. PATENT DOCUMENTS

| | | |
|---|---|---|
| 2012/0071922 A1 | 3/2012 | Shanley et al. |
| 2012/0078270 A1 | 3/2012 | Shanley et al. |
| 2012/0114755 A1 | 5/2012 | Amadio et al. |
| 2012/0150225 A1 | 6/2012 | Burkhart et al. |
| 2012/0165868 A1 | 6/2012 | Burkhart et al. |
| 2012/0258086 A1 | 10/2012 | Long et al. |
| 2012/0282235 A1 | 11/2012 | Ohashi et al. |
| 2012/0283831 A1 | 11/2012 | Murray |
| 2013/0012755 A1 | 1/2013 | Slayton |
| 2013/0110137 A1 | 5/2013 | Nicolo et al. |
| 2013/0158597 A1* | 6/2013 | Hernandez ......... A61B 17/0401 606/232 |
| 2013/0274769 A1 | 10/2013 | Bonutti et al. |
| 2014/0081209 A1 | 3/2014 | Story et al. |
| 2014/0107699 A1 | 4/2014 | Thompson |
| 2014/0276640 A1 | 9/2014 | McGee |
| 2014/0288592 A1 | 9/2014 | Hussain et al. |
| 2015/0025552 A1 | 1/2015 | Stoll |
| 2015/0038941 A1 | 2/2015 | Nebosky et al. |
| 2015/0119934 A1 | 4/2015 | Shluzas et al. |
| 2016/0045534 A1 | 2/2016 | Buckley et al. |

OTHER PUBLICATIONS

DePuy Mitek, Inc., "HealixTi—Dual Thread Suture Anchor with Titanium," Brochure. 2009.

DePuy Mitek, Inc., "Versalok—Surgical Technique for Rotator Cuff Repair," Brochure. 2007.

* cited by examiner

METHODS, DEVICES, AND SYSTEMS FOR BLOOD FLOW

CROSS REFERENCE

The present application is a divisional of U.S. application Ser. No. 15/148,464 entitled "Methods, Systems, And Devices For Blood Flow" filed May 6, 2016, which is hereby incorporated by reference in its entirety.

FIELD

The present disclosure relates generally to methods, systems, and devices for blood flow.

BACKGROUND

Soft tissues, such as ligaments, tendons, and muscles, are attached to a large portion of the human skeleton. In particular, many ligaments and tendons are attached to the bones which form joints, such as shoulder and knee joints. A variety of injuries and conditions require attachment or reattachment of a soft tissue to bone and/or surrounding tissue. For example, when otherwise healthy tissue has been torn away from a bone, surgery is often required to reattach the tissue to the bone to allow healing and a natural reattachment to occur.

One example of otherwise healthy tissue being torn away from a bone is a rotator cuff tear in which a shoulder rotator cuff tendon is partially or completely torn from a humerus. Surgery to reattach the rotator cuff tendon to the humerus has a failure rate as high as 40%. One way that has been developed to help reduce this failure rate is to add blood to the repair site to aid in and improve the healing process, as blood includes healing factors. One method to add blood is to decorticate or otherwise scuff the bone having the tendon attached thereto to induce some bleeding in the bone. Another method to add blood is to create microfracture holes in the bone having the tendon attached thereto to cause blood to "weep" from the microfracture holes. However, the blood clots within a short amount of time after the decortication, scuffing, or microfracture, typically within minutes or hours, so there is a limited amount of blood added to the repair site, which may limit the added blood's healing effects, and the blood is only added for a short time after the bone is decorticated, scuffed, or microfractured during the performance of the surgical procedure, which may not promote long term healing.

Accordingly, there remains a need for improved methods and devices for methods, systems, and devices for blood flow.

SUMMARY

In general, methods, systems, and devices for blood flow are provided.

In one aspect, a surgical device is provided that in one embodiment includes a biocompatible tubular member configured to be implanted in a bone of a patient. The tubular member has a solid sidewall defining an inner lumen extending through the tubular member such that blood can flow into the inner lumen through a first open end of the inner lumen and out of the inner lumen through a second open end of the inner lumen. The tubular member includes an anti-coagulation agent on the solid sidewall.

The surgical device can vary in any number of ways. For example, the inner lumen can be open and free of occlusions. For another example, the inner lumen can have a bioabsorbable material disposed therein that occludes the inner lumen such that the blood cannot flow out of the inner lumen through the second open end of the inner lumen until the bioabsorbable material has been at least partially absorbed by the patient's body. For yet another example, the tubular member can include a retaining member configured to engage the bone in which the tubular member is implanted to retain the tubular member within the bone. For still another example, the anti-coagulation agent can be coated on a surface of the solid sidewall. For another example, the anti-coagulation agent can be impregnated in a material forming the solid sidewall. For still another example, the anti-coagulation agent can include at least one of heparin, heparin sulfate, warfarin, hirudin, hirulog, coumarin, phosphorylcholine, indiandione, antithrombin III, bemiparin, dalteparin, danaparoid, enoxaparin, nadroparin, parnaparin, reviparin, sulodexide, tinzaparin, anticoagulant citrate dextrose solution A (ACD-A), ethylenediaminetetraacetic acid (EDTA), citrate, oxalate, a factor Xa inhibitor, and a thrombin inhibitor. For another example, the tubular member can be bioabsorbable. For yet another example, the tubular member can be non-bioabsorbable. For still another example, the tubular member can have a first retaining member configured to engage the bone in which the tubular member is implanted to resist distal advancement of the tubular member into the bone, and the tubular member can have a second retaining member spaced apart from the first retaining member and configured to engage the bone in which the tubular member is implanted to resist proximal advancement of the tubular member from the bone.

For another example, the inner lumen can have a plug removably disposed therein that occludes the inner lumen such that the blood cannot flow out of the inner lumen through the second open end of the inner lumen until the plug is removed from the inner lumen, and the plug can be configured to be implanted in the patient with the tubular member. In at least some embodiments, the plug can be made from an energy activated material disposed therein that occludes the inner lumen until the energy activated material is activated by application of energy thereto. In at least some embodiments, the plug can be a knitted material that occludes the inner lumen until the knitted material is pulled to cause the knitted material to unravel. In at least some embodiments, the plug can have a suture extending therefrom. The suture can be configured to extend from inside the patient's body to outside the patient's body and to be pulled from outside the patient's body and thereby remove the plug from the inner lumen of the tubular member.

In another embodiment, a surgical device includes a biocompatible anchor configured to be implanted in a bone of a patient. The anchor has at least one bone-engaging surface feature on an exterior surface thereof that is configured to engage the bone to secure the anchor in the bone. The anchor has an inner lumen extending therethrough such that blood can flow into the inner lumen through a first open end of the inner lumen and out of the inner lumen through a second open end of the inner lumen when the anchor is implanted in the bone. The anchor includes an anti-coagulation agent.

The surgical device can have any number of variations. For example, the anti-coagulation agent can be coated on a surface of the anchor. For another example, the anti-coagulation agent can be impregnated in a material forming the anchor. For yet another example, the anti-coagulation agent can include at least one of heparin, heparin sulfate, warfarin, hirudin, hirulog, coumarin, phosphorylcholine, indiandione, antithrombin III, bemiparin, dalteparin, danaparoid, enoxaparin, nadroparin, parnaparin, reviparin, sulodexide, tinzaparin, anticoagulant citrate dextrose solution A (ACD-A), ethylenediaminetetraacetic acid (EDTA), citrate, oxalate, a factor Xa inhibitor, and a thrombin inhibitor. For still another example, a suture coated with or impregnated with an anti-coagulation agent can be coupled to the anchor. For another example, the anchor can have a solid sidewall defining an inner lumen through which the blood flows. For yet another example, the anchor can have at least one hole formed through a sidewall thereof, and the at least one hole can be in communication with the inner lumen such that the blood can flow into the inner lumen through the hole.

In another aspect, a surgical method is provided that in one embodiment includes forming a hole in a bone of a patient in a soft tissue repair procedure, and implanting an implant in the hole. The implant includes an anti-coagulation agent. The implanted implant allows blood to flow therethrough.

The surgical method can vary in any number of ways. For example, the implant can be an anchor, and the anchor can have at least one bone-engaging surface feature on an exterior surface thereof that engages the bone to secure the anchor in the hole. For another example, the implant can be a tubular member, and the inner lumen can be open and free of occlusions when the implant is implanted in the hole such that the blood is allowed to begin flowing through the implanted implant before completion of the soft tissue repair procedure. For still another example, the method can include implanting an anchor in the bone at a site a distance away from a site where the implant is implanted, and the implant can be a tubular member that is not connected to the anchor with any implanted matter. For another example, the implant can have a solid sidewall defining an inner lumen through which the blood flows. For yet another example, the implant can have at least one hole formed through a sidewall thereof, and the at least one hole can be in communication with an inner lumen of the implant through which the blood flows such that the blood can flow into the inner lumen through the hole.

For yet another example, the implant can be a tubular member, and the inner lumen can be occluded when the implant is implanted in the hole such that the blood is prevented from flowing through the implanted implant until a selected amount of time has lapsed after completion of the soft tissue repair procedure. The method can also include removing a plug from within the inner lumen of the implanted tubular member and thereby allow blood to begin flowing through the implanted tubular member, or the implanted tubular member can have bioabsorbable material disposed in the inner lumen that occludes the inner lumen until the bioabsorbable material is at least partially absorbed by the patient's body after the selected amount of time has lapsed after completion of the soft tissue repair procedure.

BRIEF DESCRIPTION OF DRAWINGS

This invention will be more fully understood from the following detailed description taken in conjunction with the accompanying drawings, in which.

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

Various exemplary methods, systems, and devices for blood flow are provided. In general, an implant can be configured to be implanted in bone and to delay clotting of blood flowing from the bone. The implant can include an anti-coagulation agent to delay the clotting of the blood. The anti-coagulation agent can be a coating on the implant, can be natural to a material forming the implant, or can be impregnated into a material forming the implant. Although the anti-coagulant agent can be formed on a portion of the implant over which blood flows, the anti-coagulant agent can be present on an entire surface of the implant. In an exemplary embodiment, the implant is implanted in a bone in a surgical procedure for securing a soft tissue to bone, such as a rotator cuff repair procedure or an anterior cruciate ligament (ACL) repair procedure. The implant delaying the clotting of blood flowing from the bone may lengthen an amount of time the blood flows from the bone (as compared to the implant being implanted without the implant including the anti-coagulation agent and as compared to the implant not being implanted at all), which may aid in and improve the healing process by increasing an amount of blood that flows to the repair site and hence increasing a chance of the surgical procedure's success. The implant delaying the clotting of blood flowing from the bone may allow the blood to begin flow at a selected time after the surgical procedure has ended, which may aid in and improve the healing process by adding blood flow to the repair site at a time subsequent to when blood would have already clotted if the blood flow had begun during the surgical procedure (e.g., by decorticating, scuffing, or microfracturing the bone during the surgical procedure to induce blood flow).

The implants described herein can include any of a variety anti-coagulation or nonthrombogenic agents. Exemplary anti-coagulation agents include heparin, heparin sulfate, warfarin, hirudin, hirulog, coumarin, phosphorylcholine, indiandione, antithrombin III, bemiparin, dalteparin, danaparoid, enoxaparin, nadroparin, parnaparin, reviparin, sulodexide, tinzaparin, anticoagulant citrate dextrose solution A (ACD-A), ethylenediaminetetraacetic acid (EDTA), citrate, oxalate, factor Xa inhibitors, thrombin inhibitors, and other factor inhibitors or derivatives thereof. The implant's anti-coagulation agent can include a single anti-coagulation agent or a combination of multiple anti-coagulation agents.

The implants described herein can be made from any of a variety of materials. In some embodiments, the implant can be made from a non-bioabsorbable material (a single non-bioabsorbable material or a combination of multiple non-bioabsorbable materials) such that the implant is non-bioabsorbable. Exemplary non-bioabsorbable materials include polyetheretherketone (PEEK), polysulfone, polyester, silicone, and metals (e.g., stainless steel, titanium, etc.). In other embodiments, the implant can be made from a bioabsorbable material (a single bioabsorbable material or a combination of multiple bioabsorbable materials) such that the implant is bioabsorbable. A rate of a bioabsorbable implant's absorption can be tailored based on a size (length and/or diameter) of the implant and a type of bioabsorbable material forming the implant since different materials can absorb at different rates. Exemplary bioabsorbable materials include polylactic acid (PLA), polyglycolic acid (PGA), Biocryl® Rapide available from DePuy Mitek of Raynham, Mass., a resorbable metal (e.g., magnesium, zinc, iron, and alloys thereof), aliphatic polyesters, poly(amino acids), copoly(ether-esters), polyalkylene oxalates, polyamides, tyrosine derived polycarbonates, poly(iminocarbonates), polyorthoesters, polyoxaesters, polyamidoesters, polyoxaesters containing amine groups, poly(anhydrides), polyphosphazenes, polyurethanes, poly(ether urethanes), poly(ester urethanes), poly(propylene fumarate), poly(hydroxyalkanoate) and polydioxanone (PDS). Examples of aliphatic polyesters include homopolymers and copolymers of lactide (which includes lactic acid, D-, L- and meso lactide); glycolide (including glycolic acid); epsilon-caprolactone; p-dioxanone (1,4-dioxan-2-one); trimethylene carbonate (1,3-dioxan-2-one); alkyl derivatives of trimethylene carbonate; delta-valerolactone; beta-butyrolactone; gamma-butyrolactone; epsilon-decalactone; hydroxybutyrate; hydroxyvalerate; 1,4-dioxepan-2-one (including its dimer 1,5,8,12-tetraoxacyclotetradecane-7,14-dione); 1,5-dioxepan-2-one; 6,6-dimethyl-1,4-dioxan-2-one; 2,5-diketomorpholine; pivalolactone; alpha,alpha diethylpropiolactone; ethylene carbonate; ethylene oxalate; 3-methyl-1,4-dioxane-2,5-dione; 3,3-diethyl-1,4-dioxan-2,5-dione; 6,6-dimethyl-dioxepan-2-one; 6,8-dioxabicycloctane-7-one, and polymer blends thereof. Additional examples of polymer or polymer blends include a polydioxanone, a polyhydroxybutyrate-co-hydroxyvalerate, polyorthocarbonate, a polyaminocarbonate, and a polytrimethylene carbonate. The aliphatic polyesters can be homopolymers or copolymers (random, block, segmented, tapered blocks, graft, triblock, etc.) having a linear, branched or star structure. Whether bioabsorbable or non-bioabsorbable, the implants described herein are biocompatible to allow for their safe implantation in patients.

The implants described herein can include a biocompatible ceramic material. Exemplary biocompatible ceramic materials include hydroxyapatite, alpha-tricalcium phosphate, beta-tricalcium phosphate, bioactive glass, calcium phosphate, calcium sulfate, calcium carbonate, xenogeneic and allogeneic bone material, and combinations thereof. Exemplary bioactive glass materials include silicates containing calcium phosphate glass, and calcium phosphate glass with varying amounts of solid particles added to control resorption time. Exemplary compounds that can be incorporated into the calcium phosphate bioactive glass include, magnesium oxide, sodium oxide, potassium oxide, and combinations thereof.

Figure 1:
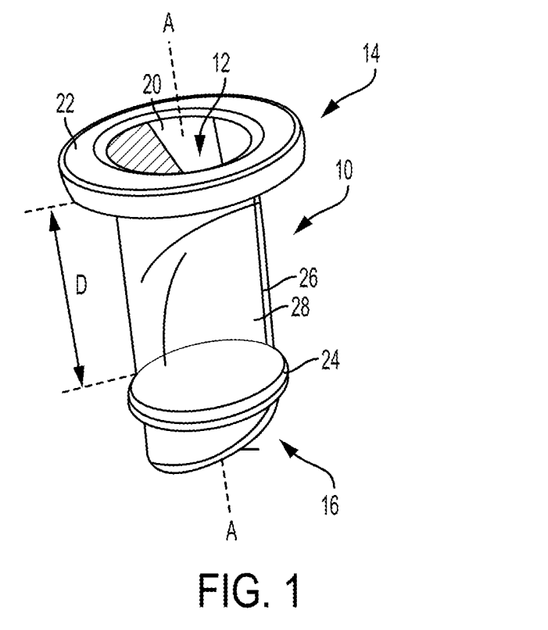
FIG. 1 is a perspective view of one embodiment of an implant.
Figure 2:
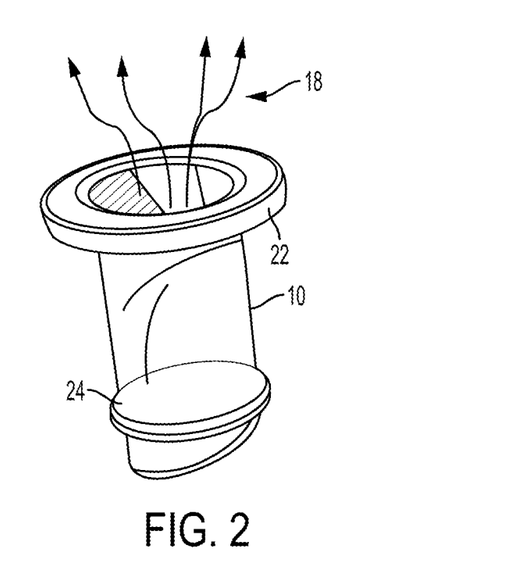
FIG. 2 is another perspective view of the implant of FIG. 1 with directional flow arrows.

FIG. 1 illustrates one embodiment of an implant 10 configured to be implanted in bone and to delay clotting of blood flowing from the bone. The implant 10 is a tubular member in the form of a tube and has an inner lumen 12 extending between proximal and distal ends 14, 16 thereof. The proximal and distal ends 14, 16 are thus open ends. The inner lumen 12 allows fluid (e.g., blood) to flow through the implant 10 when the implant 10 is implanted in a body of a patient (e.g., in a bone of a patient). Arrows 18 in FIG. 2 illustrate a distal-to-proximal direction of possible fluid flow through the implant 10. Fluid flow through the implant 10 in use is discussed further below.

The inner lumen 12 is open and free of occlusions. The inner lumen 12 may thus provide a continuous flow path through the implant 10 and may do so immediately upon implantation in a body of a patient, which may allow fluid to begin immediately flowing through the implant 10. The inner lumen 12 is defined by an inner surface 20 of the implant 10 (e.g., an inner sidewall thereof). The inner lumen 12 has a cylindrical shape and a circular cross-sectional shape in this illustrated embodiment, which may facilitate fluid flow therethrough and/or help prevent the inner lumen 12 from clogging. However, other shapes (e.g., cone-shaped, etc.) and other cross-sectional shapes (e.g., oval cross-sectional shape, etc.) are possible. The inner surface 20 is solid. The solid nature of the inner surface 20 allows that, once fluid enters the inner lumen 12 through either the inner lumen's open proximal end or open distal end, the fluid cannot exit the implant 20 through the inner surface 20 (e.g., through pore(s) or window(s) formed in the inner surface 20). Instead, the fluid can only exit the inner lumen 12 through the open proximal end or open distal end. Similarly, the solid nature of the inner surface 20 provides that fluid can only enter the inner lumen 12 through the open proximal end or the open distal end. Fluid may thus predictably flow through the inner lumen 12 and thereby help ensure that the fluid flows to an intended site (e.g., that blood flows through the inner lumen 12 to an intended tissue repair site). The inner surface 20 is smooth and free of protrusions, indentations, and other obstructions thereon or therein, which may facilitate fluid flow through the inner lumen 12 and/or help prevent the inner lumen 12 from clogging.

In other embodiments, an inner surface of an implant that defines an inner lumen of the implant can have one or more openings formed therethrough. The one or more openings can each be in communication with the inner lumen. Fluid can thus flow into the inner lumen through the one or more openings. The implant can have an open distal end such that fluid can enter the inner lumen through an opening at the open distal end and through the one or more openings, or the implant can have a closed distal end such that fluid cannot enter the inner lumen through the implant's distal end but can enter the inner lumen through the one or more side openings of the implant.

Referring again to FIG. 1, the inner lumen 12 is straight and is aligned with a longitudinal axis A of the implant 10. The inner lumen 12 can, however, be offset radially from the longitudinal axis A and/or be curved relative to the longitudinal axis A.

The implant 10 includes at least one retaining member configured to engage a bone in which the implant 10 is implanted to retain the implant 10 therein. The retaining member(s) can have a variety of sizes, shapes, and configurations. In this illustrated embodiment, the implant 10 includes a proximal retaining member 22 and a distal retaining member 24.

The proximal retaining member 22 is configured to prevent the implant 10 from moving distally once the proximal retaining member 22 engages the matter in which the implant 10 is implanted (e.g., engages a proximal surface of a bone having a hole formed therein in which the implant 10 is disposed). In other words, the proximal retaining member 22 is configured to prevent the implant 10 from advancing too far distally in bone (or other matter in which the implant 10 is implanted), which may also help a surgeon or other user implanting the implant 10 know when the implant 10 has been fully distally advanced into the bone (or other matter). A distal surface of the proximal retaining member 22 is configured to engage the matter. The proximal retaining member 22 extends radially outward from the implant's proximal end 14, thereby allowing the proximal end 14 of the implant 10 to have a diameter that is greater than a diameter of a body 26 of the implant 10. The body 26 can thus be configured to be disposed in matter in which the implant 10 is implanted while the proximal retaining member 22 remains outside of the matter. The proximal retaining member 22 is in the form of a flange extending radially outward from the proximal end 14 of the implant 10. The flange has a circular ring shape and extends around an entire perimeter of the implant's proximal end 14. The flange can, however, have other shapes (e.g., oval, triangular, etc.) and can be discontinuous around the perimeter of the implant's proximal end 14 (e.g., a series of independent flange members extending radially outward from the implant's proximal end 14, a single tab extending radially outward from the implant's proximal end 14, etc.). The proximal retaining member 22 extending around the entire perimeter of the implant's proximal end 14 may help ensure that the proximal retaining member 22 engages a surface of the matter (e.g., bone) in which the implant 10 is implanted.

The distal retaining member 24 is configured to prevent the implant 10 from moving proximally once the distal retaining member 24 engages the matter in which the implant 10 is implanted (e.g., engages a distal surface of a bone having a hole formed therein in which the implant 10 is disposed). Depending on use of the implant 10, the distal retaining member 24 can also be configured to prevent the implant 10 from moving distally once the distal retaining member 24 engages the matter in which the implant 10 is implanted. In other words, if the distal retaining member 24 is contained within the matter in which the implant 10 is implanted, as opposed to being located outside of the matter like the proximal retaining member 22, the distal retaining member 24 can be configured to prevent both proximal and distal movement of the implant 10 within the matter. The distal retaining member 24 is in the form of a protrusion extending radially outward from the body 26 of the implant 10 near the implant's distal end 16. The protrusion has a circular ring shape and extends around an entire perimeter of the implant's body 26. The protrusion can, however, have another shape (e.g., oval, triangular, etc.) and can be discontinuous around the perimeter of the implant's body 26 (e.g., a series of independent protrusions extending radially outward from the implant's body 26, a single protrusion extending radially outward from the implant's body 26, etc.).

The proximal and distal retaining members 22, 24 are configured to cooperate to retain the implant 10 within the matter in which the implant 10 is implanted. In other words, the proximal retaining member 22 is configured to prevent distal movement of the implant 10 within the matter and the distal retaining member 24 is configured to prevent proximal movement 10 of the implant 10 within the matter (and, in at least some embodiments, to also prevent distal movement 10 of the implant 10 within the matter). In an exemplary embodiment, a distance D between the proximal and distal retaining members 22, 24 corresponds to a depth of cortical bone of a bone in which the implant 10 may be implanted. In this way, the implant 10 can be configured to "trap" the cortical bone between the proximal and distal retaining members 22, 24, thereby allowing the implant 10 to grip the harder cortical bone rather than the softer cancellous bone that underlies the cortical bone. In an exemplary embodiment, the distance D is in a range of about 0.05 to 100 mm.

The implant 10 includes both of the proximal and retaining members 22, 24 in this illustrated embodiment, but an implant can include only one of the proximal and retaining members 22, 24. Alternatively, an implant can include both of the proximal and retaining members 22, 24 and one or more additional retaining members along a length of the implant's body that are similar to the distal retaining member such that the body has a plurality of protrusions at different axial positions therealong, or an implant can lack the proximal retaining member 22 and can include the distal retaining member 24 and one or more additional retaining members along a length of the implant's body that are similar to the distal retaining member such that the body has a plurality of protrusions at different axial positions therealong. An implant having the distal retaining member 24 and one or more additional retaining members similar thereto like may help ensure that at least one retaining member securely engages the matter in which the implant is implanted.

The distal end 16 of the implant 10 can be configured to facilitate insertion of the implant 10 into matter in a distal direction, which would be the typical approach direction for the implant's implantation. The distal end 16 of the implant 10 is angled to facilitate insertion of the implant 10 into matter, e.g., into bone in which the implant 10 will be implanted. The angled distal end can be sharp to further to facilitate insertion of the implant 10 into the matter. In other embodiments, a distal end of an implant can be non-angled, similar to the proximal end 14 of the implant 10.

The implant 10 includes an anti-coagulation agent configured to prevent or delay coagulation of blood, e.g., to prevent or delay clotting. A length of time that the anti-coagulation agent prevents the blood from coagulating is generally a function of a type of the anti-coagulation agent and an amount of the anti-coagulation agent that is present, as will be appreciated by a person skilled in the art. In an exemplary embodiment, the length of time blood encountering the anti-coagulant agent flows before coagulating is in a range of about one to three hundred minutes, e.g., in a range of about four to twenty minutes, in a range of about four to fifteen minutes, in a range of about fifteen to twenty minutes, etc.

The anti-coagulation agent is coated on the implant 10 in the illustrated embodiment. The anti-coagulation agent is coated on an entirety of the implant's exposed surface, including on the inner surface 20 and on the implant's outer surface 28, which may help ensure that any blood that comes into contact with the implant 10 is encouraged to flow and not clot. Similarly, each of an implant including an anti-coagulation agent as natural to a material forming the implant and an implant including an anti-coagulation agent impregnated into a material forming the implant encourages any blood that comes into contact with the implant to flow and not clot. In other embodiments, an implant can have an anti-coagulation agent coated on only a partial portion thereof. For example, the anti-coagulation agent can be coated only on an inner surface of an implant (e.g., the inner surface 20 of the implant 10), which may help encourage blood flowing through the implant's inner lumen toward a tissue repair site to not clot after exiting the implant. Similarly, an implant including an anti-coagulation agent as natural to a material forming the implant can include that material in only a portion of the implant (such as only in the implant's body or only along an inner surface defining an implant's inner lumen), and an implant including an anti-coagulation agent impregnated into a material forming the implant can include that material in only a portion of the implant (such as only in the implant's body or only along an inner surface defining an implant's inner lumen). The coating of the anti-coagulation agent, whether coated on an entirety of the implant's exposed surface or on only a partial portion of the implant's exposed surface, is, in at least some embodiments, a gradient coating.

In use, the implant 10 and other implants disclosed herein can be used in any number of a variety of surgical procedures and can be driven into a bone in the surgical procedure. For example, the surgical procedure can include a soft tissue repair procedure for securing a soft tissue to bone, such as a rotator cuff repair, Achilles, or ACL repair procedure.

In general, a surgical procedure can be performed as it would be typically performed on a patient except that an implant is implanted in a bone adjacent a target site in which blood flow is desired to facilitate healing, such as in a bone adjacent to a soft tissue reattachment site. A single implant can be implanted in the patient, or a plurality of implants can be implanted in the patient. If a plurality of implants are implanted, each of the implants can be identical to one another or any one or more of the implants can differ from any one or more of the other implants, e.g., have different sizes, include different anti-coagulation agents, etc.

Figure 3:
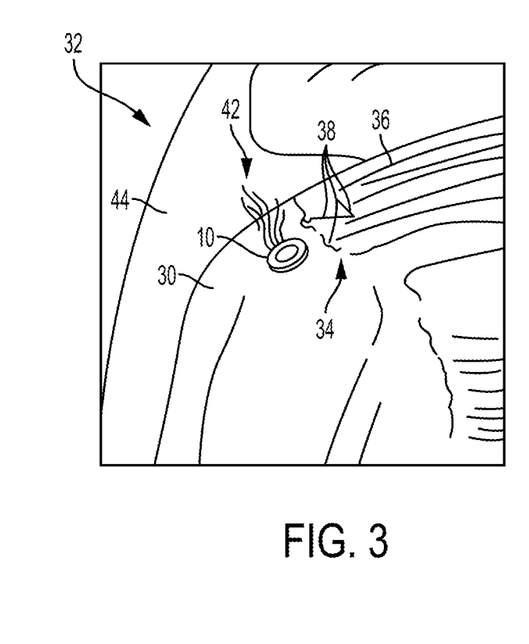
FIG. 3 is a perspective partially transparent view of one embodiment of the implant of FIG. 1 implanted in a patient.
Figure 4:
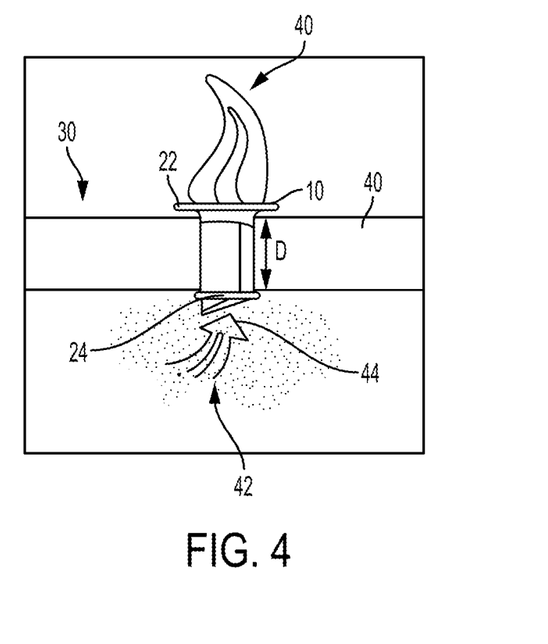
FIG. 4 is a side partially cross-sectional view of the implant of FIG. 3 implanted in the patient.

FIGS. 3 and 4 illustrate one embodiment of use of the implant 10. Other implants disclosed herein can be similarly used. FIGS. 3 and 4 illustrate the implant 10 implanted in a humerus 30 of a patient 32 in rotator cuff repair. Only one of the implants 10 is implanted in the bone 30, but as mentioned above, more than one implant can be implanted. When a plurality of implants are implanted, at least one of the implants can have an unoccluded inner lumen, like the implant 10, to allow for blood flow therethrough at a time of surgery, and at least one of the implants can have an occluded lumen (for example, the implants of FIGS. 5-8 discussed below) to allow for blood flow therethrough at a time after the surgery. More blood may thus be allowed to flow at the soft tissue reattachment site 34 throughout the healing process. Alternatively, when a plurality of implants are implanted, all of the implants can have an occluded lumen and be configured to have its lumen unoccluded at different times post-surgery, e.g., by plugs in the various inner lumens being removed at different times manually or naturally via absorption.

As mentioned above, the rotator cuff procedure can be performed as it would be typically performed on a patient except that the implant 10 is implanted in a bone (the humerus 30) adjacent to the soft tissue reattachment site 34, which here is where a rotator cuff tendon 36 is secured to the humerus 30 using sutures 38 and anchors (obscured in the bone 30 under the tendon 36). The implant 10 is implanted lateral to the tendon 36, but instead the implant 30 can be implanted under the tendon 36.

In an exemplary embodiment, the implant 10 is implanted after the rotator cuff tendon 36 is secured to the humerus 30, which may allow the rotator cuff tendon 36 to be secured to the humerus 30 without the implant 10 interfering with the securing process.

FIG. 4 illustrates the distance D between the proximal and distal retaining members 22, 24 as corresponding to a depth of cortical bone 40 of the humerus 30 with the proximal retaining member 22 engaging a proximal surface of the cortical bone 40 (and hence a proximal surface of the humerus 30) and the distal retaining member 24 engaging a distal surface of the cortical bone 40. FIG. 4 also illustrates blood 42 flowing in a proximal direction, as indicated by arrow 44, through the inner lumen 12 with the blood 42 entering the implant 10 through the implant's open distal end and exiting the implant 10 through the implant's open proximal end. FIG. 3 also shows the exiting of the blood 42 from the implant 10. The blood 42 may thus flow in a direction toward the tissue reattachment site 34 and encourage healing thereat.

The implant 10 can be implanted in the humerus 30 in any of a variety of ways, as will be appreciated by a person skilled in the art. For example, the implant 10 can be advanced into the patient in a minimally invasive fashion through the patient's skin 44 and driven into the humerus 30 similar to the driving of the anchors into the humerus 30, e.g., by using a driver tool to push the implant 10 into the humerus 30.

Figure 5:
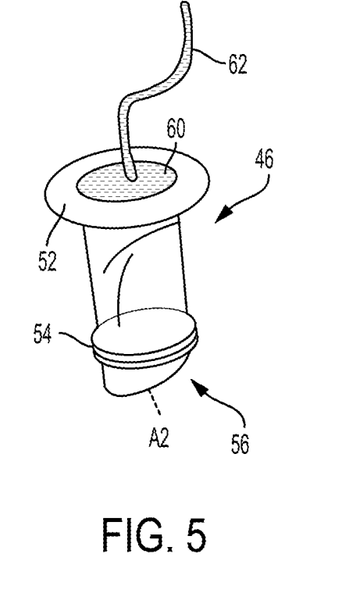
FIG. 5 is a perspective view of one embodiment of an implant including a plug disposed therein.
Figure 6:
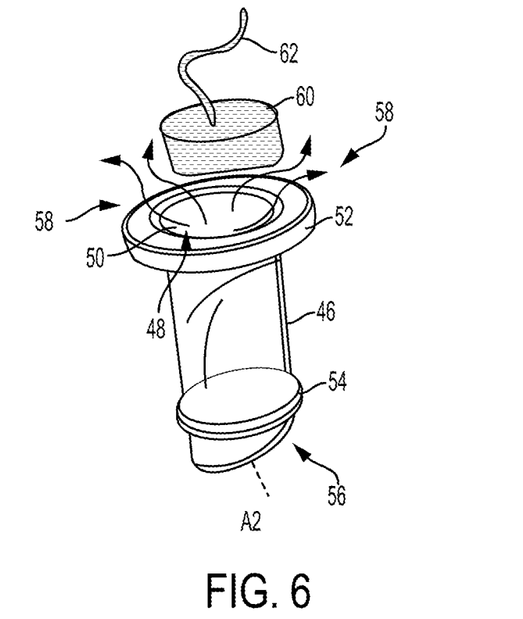
FIG. 6 is a perspective view of the implant of FIG. 5 with directional flow arrows and with the plug removed therefrom.

FIGS. 5 and 6 illustrate another embodiment of an implant 46 configured to be implanted in bone and to delay clotting of blood flowing from the bone. The implant 46 is a tubular member in the form of a tube. The implant 46 is generally configured and used similar to the implant 10 of FIG. 1, e.g., includes an inner lumen 48 defined by a solid inner surface 50 of the implant 46 and aligned with a longitudinal axis A2 of the implant 46, a proximal retaining member 52 in the form of a flange, a distal retaining member 54 in the form of a ring-shaped protrusion, an angled distal end 56, and an anti-coagulation agent in the form of a coating that coats an entirety of the implant's exposed surface.

The inner lumen 48 of the implant 46 of FIGS. 5 and 6 is occluded in a first configuration of the implant 46, shown in FIG. 5. Fluid cannot flow through open proximal and distal ends of the implant 46 in the first configuration due to the occlusion. Fluid can enter the inner lumen 48 through the implant's open distal end, but the occlusion prevents the fluid's exit from the implant 48 through the proximal open end. In other embodiments, fluid can be prevented from entering an implant's inner lumen at all due to an occlusion in the implant's inner lumen. The implant 48 is configured to move from the first configuration to a second configuration, shown in FIG. 6, in which the inner lumen 48 is not occluded. The implant 46 in the second configuration is thus like the implant 10 of FIG. 1 with its inner lumen 48 being open and free of occlusions. Arrows 58 in FIG. 6 shows a distal-to-proximal direction of possible fluid flow through the implant 46 in the second configuration. In another embodiment, the implant in the second configuration can be partially open and partially occluded so as to allow fluid flow therethrough while a portion of the plug remains in the implant's inner lumen.

The implant 46 is configured to be implanted in a patient in the first configuration and to be moved from the first configuration to the second configuration after the implantation. The implant 46 is configured to move from the first configuration to the second configuration at a selected time after the implantation of the implant 46 in a patient. Fluid can thus begin to flow through the implant 46 at a selected time, which may allow blood flow at an intended surgical site to begin at a time selected by a doctor or other medical professional as desired based on any one or more factors, such as the patient's medical history, the doctor's/professional's personal preference, etc. In at least some embodiments, the selected time is after completion of the surgical procedure in which the implant 46 is implanted in a patient. The blood flow may thus begin post-surgery, which may help accelerate and/or otherwise improve healing post-surgery. The selected time can vary. For example, the selected time can be a time in a range of one day to several days, in a range of one day to one week, one week, or in a range of two weeks to four weeks (e.g., two weeks after surgery, twenty days after surgery, four weeks after surgery, etc.). In other embodiments, the selected time is at or near an end of the surgical procedure in which the implant 46 is implanted in a patient, e.g., as a last step of the procedure before access to the patient is closed (e.g., an access portal incision into the patient is closed, etc.). The blood flow may thus begin as late as possible in the surgery.

As shown in FIG. 5, the inner lumen 48 of the implant 46 is occluded by a plug 60 that is at least partially disposed in the inner lumen 48. The plug 60 is fully contained within the inner lumen 48 in this illustrated embodiment. The plug 60 being fully contained within the inner lumen 48 may help minimize a profile of the implant 48 and thereby help prevent the implant 48 from poking into, rubbing against, or otherwise disturbing tissue structures near the implant 48 when implanted in a patient. In other embodiments, a plug of an implant can be partially outside of the implant when the implant is in its first configuration, e.g., a proximal portion of the plug can extend proximally beyond a proximal end of the implant. The plug being partially contained within the inner lumen may make the plug easier to remove from the implant.

The plug 60 can have a variety of sizes, shapes, and configurations. In general, the plug 60 has a size and shape that allows the plug 60 to occlude the inner lumen 48 so fluid cannot flow through the inner lumen 48 when the plug 60 is disposed therein. The inner lumen 48 in this illustrated embodiment has a cylindrical shape and a circular cross-sectional shape, so the plug 60 has a corresponding cylindrical shape and circular cross-sectional shape. The plug 60 has a length that is less than a length of the inner lumen 48, as shown in FIG. 6, which may make the plug 60 easier to remove from the inner lumen 48.

The plug 60 is configured to be removed from the inner lumen 48 at the selected time to move the implant 46 from the first configuration to the second configuration. The plug 60 is attached to a suture 62 that extends proximally therefrom, and hence extends proximally from the implant 46. The suture 62 is configured to be manipulated by a user (e.g., a surgeon, a nurse, etc.), e.g., pulled in a proximal direction, to remove the plug 60 from the inner lumen 48. The suture 62 has a length that is long enough to allow the suture 62 to extend from the plug 60 implanted in a body of a patient and through a skin of the patient such that a proximal portion of the suture 62 is located outside of the patient. The suture 62 can thereby be manipulated from outside the patient's body to remove the plug 60 from the inner lumen 48, e.g., by pulling on the proximal portion of the suture 62, and allow blood to flow through the implant 46. The suture 62 can be trimmed in length outside of the patient's body such that only a short length of suture is located outside the patient's body, which may help prevent the suture 62 from being accidentally pulled before the selected time, even if the proximal portion of the suture 62 is covered on the patient's skin, such as with a bandage.

The suture 62 can be attached to the plug 60 in any of a variety of ways, e.g., being molded therein, by being glued thereto with adhesive, by being heat-melted thereto, by being tied thereto, etc. The suture 62 includes a single strand, but in other embodiments a suture attached to a plug can include multiple strands. The plug 60 is attached to only one suture 62, but in other embodiments, a plug can be attached to multiple sutures that each extend proximally from the plug and is configured to be manipulated to remove the plug from the implant.

In an exemplary embodiment, the plug 60 is made from a non-bioabsorbable material (a single material or a combination of multiple materials) such that the plug 60 is non-bioabsorbable, and the suture 62 is made from a non-bioabsorbable material (a single material or a combination of multiple materials) such that the suture 62 is non-bioabsorbable. The inner lumen 48 may thus become unoccluded at a selected time, e.g., the implant 46 can be moved from the first configuration to the second configuration at a selected time, thereby allowing the time to be selected by a doctor or other medical professional as desired for the particular patient in which the implant 46 is implanted based on any one or more factors, such as the patient's medical history, the doctor's/professional's personal preference, etc. In other embodiments, the plug 60 and/or the suture 62 can be made from a bioabsorbable material (a single material or a combination of multiple materials) so as to be bioabsorbable. The plug 60 and suture 62 being bioabsorbable allows the plug 60 and suture 62 to be removed from the inner lumen 48 at a selected time before a known absorption time of the plug 60 and suture 62 or to be left in the inner lumen 48 to dissolve within the patient's body at the known absorption time.

In another embodiment, an implant similar to the implant 46 of FIG. 5 has a plug partially disposed in an inner lumen of the implant and extending proximally beyond the implant's proximal end. The plug has a length that is long enough to allow the plug to extend from the plug implanted in a body of a patient and through a skin of the patient such that a proximal portion of the plug is located outside of the patient. The plug is configured to configured to be manipulated by a user (e.g., a surgeon, a nurse, etc.), e.g., pulled in a proximal direction, to remove the plug from the inner lumen of the implant. Thus, instead of having a suture attached thereto like the plug 60 and the suture 62 of FIGS. 5 and 6, the plug itself is configured to extend from the patient's body to allow removal of the plug from the implant's inner lumen to begin blood flow therethrough. In an exemplary embodiment, the plug is made from a knitted material configured to narrow in diameter when pulled so as to allow the plug to occlude the implant's inner lumen (e.g., in a first configuration of the implant) and then, when pulled, unravel to narrow in diameter and not occlude the implant's inner lumen (e.g., in a second configuration of the implant) and be removed from the inner lumen. The plug can thus be configured to be pulled out of the patient's body through the patient's skin with the plug in its unraveled state.

Figure 7:
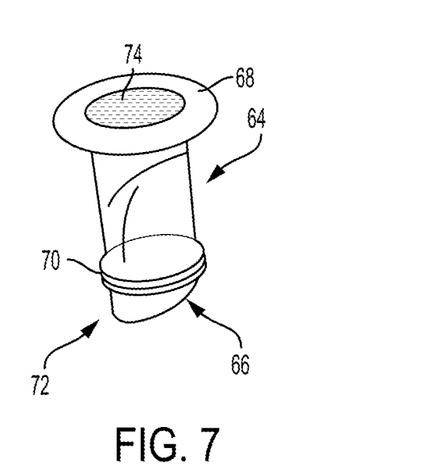
FIG. 7 is a perspective view of another embodiment of an implant including a plug disposed therein.
Figure 8:
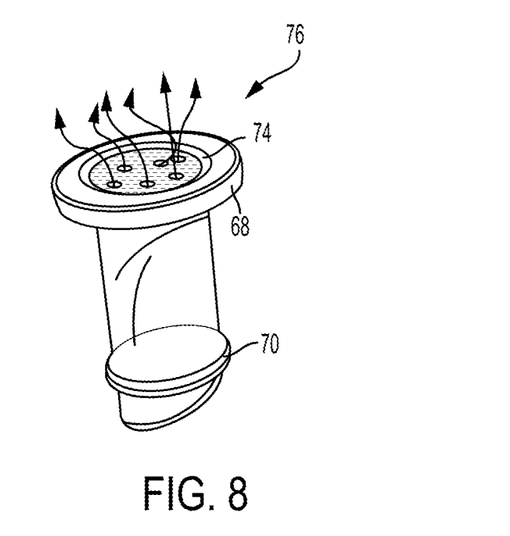
FIG. 8 is a perspective view of the implant of FIG. 7 with directional flow arrows and with the plug removed therefrom.

FIGS. 7 and 8 illustrate another embodiment of an implant 64 configured to be implanted in bone and to delay clotting of blood flowing from the bone. The implant 64 is a tubular member in the form of a tube. The implant 64 is generally configured and used similar to the implant 10 of FIG. 1, e.g., includes an inner lumen 66 defined by a solid inner surface (obscured in FIGS. 7 and 8) of the implant 64 and aligned with a longitudinal axis A3 of the implant 64, a proximal retaining member 68 in the form of a flange, a distal retaining member 70 in the form of a ring-shaped protrusion, an angled distal end 72, and an anti-coagulation agent in the form of a coating that coats an entirety of the implant's exposed surface.

The implant 64 is configured to be implanted in a patient in a first configuration in which the inner lumen 66 is occluded such that fluid cannot flow therethrough and to be moved after the implantation from the first configuration to a second configuration in which the inner lumen 66 is at least partially unoccluded such that fluid can flow therethrough. The first configuration of the implant 64 is similar to the first configuration of the implant 46 of FIG. 5 in that fluid cannot flow through open proximal and distal ends of the implant 64 in the first configuration due to the occlusion. The second configuration is a transitional state in which the occlusion gradually dissipates such that the inner lumen 66 becomes more unobstructed over time such that more fluid can flow through the inner lumen 66 over time. Eventually, the inner lumen 66 becomes fully unoccluded in the second configuration similar to the second configuration of the implant 46 of FIG. 6.

As shown in FIG. 7, the inner lumen 66 of the implant 64 is occluded by a plug 74 that is at least partially disposed in the inner lumen 66. The plug 74 is fully contained within the inner lumen 66 in this illustrated embodiment, but similar to that discussed above regarding the plug 60 of FIGS. 5 and 6, in other embodiments, a plug can be partially outside of an implant. The plug 74 is made from a bioabsorbable material (a single material or a combination of multiple materials) so as to be bioabsorbable. The plug 74 is thus configured to dissolve within a patient's body so as to gradually dissipate from within the inner lumen 66 at a known absorption time accordingly to a known absorption rate of the material(s) forming the plug 74. FIG. 8 shows a plurality of areas (six) in the plug 74 in which material forming the plug 74 has dissolved to allow fluid flow, as shown by directional arrows 76. The plug 74 being bioabsorbable allows the plug 74 to fully dissolve within the patient's body, as opposed to remaining the patient's body until such time it is manually removed therefrom, which may subject the patient to various risks such as injury from a loose plug within their body. The plug 74 being bioabsorbable allows the inner lumen 66 to become unoccluded at a predictable time post-surgery since an absorption rate of the material(s) forming the plug 74 will be known. A rate of the plug's absorption can be tailored based on a size of the plug 74, a size (length and/or diameter) of the inner lumen 66 in which the plug 74 is at least partially disposed, and a type of bioabsorbable material forming the plug 74 since different materials can absorb at different rates.

In another embodiment, an implant similar to the implant 64 of FIG. 7 has a plug that is at partially disposed in an inner lumen of the implant, but the plug is formed of a material configured to be activated by energy to move the implant from a first configuration in which the inner lumen is occluded to a second configuration in which the inner lumen is unoccluded. The material can be activated by the energy at a selected time after the implantation of the implant in a patient as selected by a doctor or other medical professional as desired based on any one or more factors, such as the patient's medical history, the doctor's/professional's personal preference, etc.

In an exemplary embodiment, the energy-activatable material forming the plug includes a material (a single material or a combination of multiple materials) configured to be activated by ultrasonic energy, such as high-energy focused ultrasound (HIFU) or a magnetic field for a magnetic material, such as pulsed electromagnetic field therapy (PEMF). In general, HIFU is a technique that locally heats an area within a patient's body, as will be appreciated by a person skilled in the art. This heating can cause the plug to dissolve and thereby unocclude the implant's inner lumen. Heating or ablation volumes using HIFU are traditionally on the order of 1 mm in diameter, which would be compatible with the implant. Examples of material configured to be activated by ultrasonic energy include a biomaterial configured to be shrunk by heating (such as a collagen-based structure), a polymer (such as polycaprolactone, which has a melting point of about 60 degrees Celsius), a foamed polymer configured to decrease in volume when heated, and a shape memory material (polymer or metal). The shape memory material can be configured to act as a valve within the implant's inner lumen by changing shape when activated by the energy.

An amount of energy required to dissolve the plug can vary, such as in a range of about 1 to 2 Joules. If the plug includes a thin membrane extending across the inner lumen, includes liquid to be heated to expand enough to break a seal, or to cause a shape memory material valve to open, the energy can be less than 1 Joule, and in at least some cases, substantially less than 1 Joule.

In at least some embodiments, the energy-activatable material forming the plug includes one or more cavities therein that each have contained therein an anti-coagulating agent. The implant can thus include an anti-coagulating agent in the one or more cavities and, optionally, as any one or more of a coating on at least a portion of the implant, natural to a material forming at least a portion of the implant, and impregnated into a material forming at least a portion of the implant. The anti-coagulating agent can be configured to be released from the one or more cavities when the energy-activatable material is activated.

In at least some embodiments, the plug formed of the energy-activatable material is in the form of a proximal cap sealing a proximal end of the inner lumen and a distal cap sealing a distal end of the inner lumen. An anti-coagulating agent is contained within the inner lumen between the proximal and distal caps. The implant can thus include an anti-coagulating agent in the inner lumen and, optionally, as any one or more of a coating on at least a portion of the implant, natural to a material forming at least a portion of the implant, and impregnated into a material forming at least a portion of the implant. The anti-coagulating agent can be configured to be released from the inner lumen when the energy-activatable material is activated to disrupt the proximal and distal caps either by pressure build-up in the inner lumen and/or the energy causing the proximal and distal caps to break.

Figure 9:
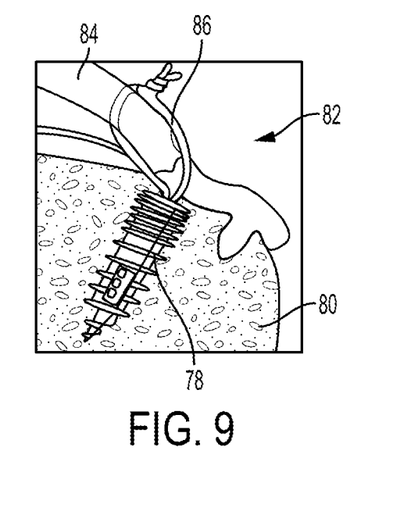
FIG. 9 is a perspective partially transparent, partially cross-sectional view of another embodiment of an implant implanted in a patient.

FIG. 9 illustrates another embodiment of an implant 78 configured to be implanted in bone and to delay clotting of blood flowing from the bone. The implant 78 is in the form of an anchor configured to be implanted in bone and having an inner lumen extending therethrough (e.g., the anchor is cannulated). Surgical procedures such as soft tissue repair procedures traditionally use one or more anchors as part of the procedure. For example, the rotator cuff repair of FIGS. 3 and 4 uses anchors, as mentioned above. Any or all of the one or more anchors used in the surgical procedures such as soft tissue repair procedures can be the implant 78 (or other implant in the form of an anchor described herein). The surgical procedure thus need not be performed any differently than traditionally performed except that the anchor(s) include an anti-coagulating agent to delay clotting of blood flowing from the bone and, optionally, bone need not be decorticated, scuffed, or microfractured to induce blood flow. The benefits of delayed blood clotting may thus be achieved without any disruption to a surgeon's preferred surgical procedure technique. The anti-coagulation agent is coated on the implant 78 in the illustrated embodiment. The coating is present on an entire surface of the implant 78, but as mentioned above, the coating can be on only a portion of the implant 78, e.g., a portion in which flowing blood is expected to flow on. However, as mentioned above, the implant 78 can instead or additionally have an anti-coagulation agent coated thereon (either on an entirety of the implant's exposed surface or on only a portion thereof), as natural to a material forming the anchor, and/or impregnated into a material forming the anchor.

As shown in FIG. 9, the implant 78 has an opening formed through a sidewall thereof. The opening is in communication with an inner lumen of the implant 78 through which fluid (e.g., blood) can flow. Fluid can thus flow into the inner lumen through the opening. The opening is located in an intermediate location of the implant 78 between proximal and distal end thereof. The proximal end of the implant 78 is open, and the distal end of the implant 78 is closed such that fluid entering the inner lumen through the opening can flow proximally and out of the open proximal end of the implant 78. The opening in this illustrated embodiment includes two openings on opposite sides of the implant 78 (one of the openings is obscured in FIG. 9), but an implant can include a single opening or more than two openings.

FIG. 9 illustrates the implant 78 implanted in a humerus 80 of a patient 82 in rotator cuff repair, but as mentioned above, the implant 78 can be used in other types of surgical procedures. Only one of the implants 78 is implanted in the bone 80, but as mentioned above, more than one implant can be implanted.

As shown in FIG. 9, the anchor 78 is secured to the rotator cuff tendon 84 with a suture 86. The suture 86 can include an anti-coagulation agent coated thereon (either on an entirety of the suture's exposed surface or on only a portion thereof), as natural to a material forming the suture 86, and/or impregnated into a material forming the suture 86. Thus, both the anchor 78 and the suture 86 can be configured to contribute to delayed blood clotting. Sutures used to secure other anchors used in the surgical procedure can similarly include an anti-coagulation agent coated thereon, as natural to a material forming the suture, and/or impregnated into a material forming the suture.

In this illustrated embodiment, the suture 86 is configured to slide through the inner lumen of the anchor 78. The inner lumen is thus unoccluded, similar to the inner lumen 12 of the implant 10 of FIG. 1, to facilitate the suture's sliding therein. In embodiments of anchors that are used with a suture that does not slide within an inner lumen of the anchor (e.g., the anchor is used with a non-sliding suture), the inner lumen of the anchor can have a plug at least partially disposed therein similar to the bioabsorbable plug 74 of FIG. 7, and the anchor and/or the plug can include an anti-coagulating agent, as discussed above.

The anchor 78 is one embodiment of an anchor that includes an anti-coagulation agent. Other exemplary embodiments of anchors that can include an anti-coagulation agent coated thereon (either on an entirety of the implant's exposed surface or on only a portion thereof), as natural to a material forming the anchor, and/or impregnated into a material forming the anchor include the Healix Advance™ anchor available from DePuy Mitek of Raynham, Mass., Healix TI™, Healix PEEK™, and Healix BR™ Dual-Threaded anchors available from DePuy Mitek of Raynham, Mass., Healix Transtend™ anchor available from DePuy Mitek of Raynham, Mass., Versalok™ anchor available from DePuy Mitek of Raynham, Mass., the anchors described in U.S. Pat. No. 8,114,128 entitled "Cannulated Suture Anchor" filed Nov. 1, 2006, the content of which is hereby incorporated by reference in its entirety, and the anchors described in U.S. Pat. No. 8,702,754 entitled "Methods For Anchoring Suture To Bone" filed Sep. 14, 2007, the content of which is hereby incorporated by reference in its entirety.

A person skilled in the art will appreciate that the methods, systems, and devices disclosed herein have application in conventional minimally-invasive and open surgical instrumentation as well application in robotic-assisted surgery.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical device, comprising:
a one-piece biocompatible anchor configured to be implanted in a bone of a patient, the anchor not being bioabsorbable, the anchor having at least one bone-engaging surface feature on an exterior surface thereof that is configured to engage the bone and thereby secure the anchor in the bone, the anchor having an inner lumen extending therethrough configured to allow blood to flow into the inner lumen through a first open end of the inner lumen and out of the inner lumen through a second open end of the inner lumen when the anchor is implanted in the bone, and the anchor including an anti-coagulation agent, the at least one bone-engaging surface feature including a first flange, which extends radially outward from a proximal end of the anchor in which the first open end is formed, and a second flange, which extends radially outward from a distal end of the anchor in which the second open end is formed, wherein the anchor has a solid sidewall defining an entire length of the inner lumen through which the blood can flow in the anchor and that thereby limits blood that flows into the inner lumen through the first open end from exiting the inner lumen only through the first open end or the second open end.

2. The device of claim 1, wherein the anti-coagulation agent is coated on a surface of the anchor.

3. The device of claim 1, wherein the anti-coagulation agent is impregnated in a material forming the anchor.

4. The device of claim 1, wherein the anti-coagulation agent includes at least one of heparin, heparin sulfate, warfarin, hirudin, hirulog, coumarin, phosphorylcholine, indiandione, antithrombin III, bemiparin, dalteparin, danaparoid, enoxaparin, nadroparin, parnaparin, reviparin, sulodexide, tinzaparin, anticoagulant citrate dextrose solution A (ACD-A), ethylenediaminetetraacetic acid (EDTA), citrate, oxalate, a factor Xa inhibitor, and a thrombin inhibitor.

5. The device of claim 1, wherein a suture coated with or impregnated with an anti-coagulation agent is coupled to the anchor.

6. The device of claim 1, wherein the anchor includes a body having a first maximum diameter, and the first flange has a second maximum diameter that is greater than the first maximum diameter.

7. The device of claim 1, wherein the flanges each extend around an entire perimeter of the body.

8. A surgical device, comprising:
a biocompatible anchor configured to be implanted in a bone of a patient with an inner lumen extending through the anchor being open and free of occlusions, the inner lumen extending through the anchor such that blood can flow into the inner lumen through a first open end of the inner lumen and out of the inner lumen through a second open end of the inner lumen when the anchor is implanted in the bone, the anchor including an anti-coagulation agent;
wherein the anchor includes a body and a flange integrally formed with the body, the flange extends radially outward from the body around an entire perimeter of the body at a fixed axial position along a longitudinal axis of the body, the body has a first maximum diameter, and the flange has a second maximum diameter that is greater than the first maximum diameter.

9. The device of claim 8, wherein the anti-coagulation agent is coated on a surface of the anchor.

10. The device of claim 8, wherein the anti-coagulation agent is impregnated in a material forming the anchor.

11. The device of claim 8, wherein the anti-coagulation agent includes at least one of heparin, heparin sulfate, warfarin, hirudin, hirulog, coumarin, phosphorylcholine, indiandione, antithrombin III, bemiparin, dalteparin, danaparoid, enoxaparin, nadroparin, parnaparin, reviparin, sulodexide, tinzaparin, anticoagulant citrate dextrose solution A (ACD-A), ethylenediaminetetraacetic acid (EDTA), citrate, oxalate, a factor Xa inhibitor, and a thrombin inhibitor.

12. The device of claim 8, wherein the anchor has a solid sidewall defining the inner lumen through which the blood flows.

13. The device of claim 8, wherein the anchor has at least one hole formed through a sidewall thereof, and the at least one hole being in communication with the inner lumen such that the blood can flow into the inner lumen through the at least one hole.

14. The device of claim 8, wherein the first open end of the inner lumen is at a proximal end of the anchor;
the second open end of the inner lumen is at a distal end of the anchor; and
the axial position of the flange is at a same axial position as the first open end of the inner lumen and surrounds the first open end of the inner lumen.

15. The device of claim 8, wherein the first open end of the inner lumen is at a proximal end of the anchor;
the second open end of the inner lumen is at a distal end of the anchor; and
the axial position of the flange is located in an intermediate portion of the body between axial positions of the first and second open ends of the inner lumen.

* * * * *